United States Patent
Liberg et al.

(10) Patent No.: US 9,956,212 B2
(45) Date of Patent: May 1, 2018

(54) QUINOLINE CARBOXAMIDES FOR USE IN THE TREATMENT OF MULTIPLE MYELOMA

(71) Applicant: Active Biotech AB, Lund (SE)

(72) Inventors: David Liberg, Lomma (SE); Anders Olsson, Lund (SE); Dmitry Gabrilovich, Villanova, PA (US); Yuliya Nefedova, Villanova, PA (US)

(73) Assignee: Active Biotech AB, Lund (SE)

( * ) Notice: Subject to any disclaimer, the term of this patent is extended or adjusted under 35 U.S.C. 154(b) by 0 days. days.

(21) Appl. No.: 15/510,728

(22) PCT Filed: Sep. 18, 2015

(86) PCT No.: PCT/EP2015/071391
§ 371 (c)(1),
(2) Date: Mar. 13, 2017

(87) PCT Pub. No.: WO2016/042112
PCT Pub. Date: Mar. 24, 2016

(65) Prior Publication Data
US 2017/0273967 A1 Sep. 28, 2017

(30) Foreign Application Priority Data
Sep. 23, 2014 (EP) .................... 14185892

(51) Int. Cl.
*A61K 31/47* (2006.01)
*A61K 31/167* (2006.01)
*C07D 215/22* (2006.01)

(52) U.S. Cl.
CPC ............ *A61K 31/47* (2013.01); *A61K 31/167* (2013.01); *C07D 215/22* (2013.01)

(58) Field of Classification Search
CPC ..... A61K 31/47; A61K 31/167; C07D 215/22
See application file for complete search history.

(56) References Cited

U.S. PATENT DOCUMENTS 6,395,750 B1 * 5/2002 Hedlund ................ A61K 31/47
514/312
9,469,876 B2 * 10/2016 Kuslich ................ C12Q 1/6886

FOREIGN PATENT DOCUMENTS

| WO | 1999/055678 A1 | 11/1999 |
|---|---|---|
| WO | 2000/003991 A1 | 1/2000 |
| WO | 2001/030758 A1 | 5/2001 |
| WO | 2003/106424 A1 | 12/2003 |
| WO | 2005/074899 A2 | 8/2005 |
| WO | 2012/004338 A1 | 1/2012 |
| WO | 2012/066478 A1 | 5/2012 |
| WO | 2012/175541 A1 | 12/2012 |
| WO | WO2012175541 | * 12/2012 |
| WO | WO 2012024543 | * 2/2014 |

OTHER PUBLICATIONS

Raymond, Cancer Chemother Parmacol, vol. 73, 1-8, 2014.*
International Search Report for corresponding International Application No. PCT/EP2015/071391 dated Nov. 11, 2015.
Written Opinion of the International Searching Authority for corresponding International Application No. PCT/EP2015/071391 dated Nov. 11, 2015.
Shen et al., "Modulation of suppressive myeloid populations by tawquinimod", Cancer Research, vol. 73, No. 8, Supplement 1, Apr. 15, 2013, p. 4746.
Jennbacken et al., "Inhibition of Metastasis in a Castration Resistant Prostate Cancer Model by the Quinoline-3-Carboxamide Tasquinimod (ABR-215050)", The Prostate, vol. 72, No. 8, Jun. 1, 2012, pp. 913-924.

* cited by examiner

*Primary Examiner* — D Margaret M Seaman
(74) *Attorney, Agent, or Firm* — Renner, Otto, Boisselle & Sklar, LLP

(57) ABSTRACT

A compound of formula (I), or a pharmaceutically acceptable salt thereof, for use in the treatment of multiple myeloma.

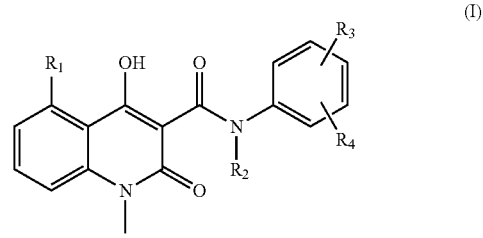

(I)

20 Claims, 4 Drawing Sheets

TASQ 30 mg/kg/day

Control

QUINOLINE CARBOXAMIDES FOR USE IN THE TREATMENT OF MULTIPLE MYELOMA

This application is a national phase of International Application No. PCT/EP2015/071391 filed Sep. 18, 2015, and claims priority to Application No. EP 14185892.8 filed Sep. 23, 2014.

FIELD OF THE INVENTION

The present invention relates to certain quinoline carboxamides for use in the treatment of multiple myeloma. More particularly, the invention relates to the compound 4-hydroxy-5-methoxy-N, 1-dimethyl-2-oxo-N-[4-(trifluoromethyl)phenyl]-1,2-dihydroquinoline-3-carboxamide (tasquinimod), or a pharmaceutically acceptable salt thereof, for use in the treatment of multiple myeloma.

BACKGROUND OF THE INVENTION

Various therapeutically active quinoline carboxamides and a method for their preparation were described in International Applications No. PCT/SE99/00676, published as WO 99/55678 and No. PCT/SE99/01270, published as WO 00/03991, which applications disclosed the utility of these compounds for the treatment of diseases resulting from autoimmunity, such as multiple sclerosis, insulin-dependent diabetes mellitus, systemic lupus erythematosus, rheumatoid arthritis, inflammatory bowel disease and psoriasis and, furthermore, diseases where pathologic inflammation plays a major role, such as asthma, atherosclerosis, stroke and Alzheimer's disease.

Processes for preparing therapeutically active quinoline carboxamides also have been described in International Application No. PCT/SE2003/000780, published as WO 03/106424 and in International Application No. PCT/EP2011/061490, published as WO 2012/004338. A deuterated form of a quinoline carboxamide is described in International Application No. PCT/EP2012/061798, published as WO 2012/175541.

Pharmaceutical compositions containing a salt of a quinoline carboxamide having enhanced stability during long-term storage at room temperature, methods for the manufacture of such compositions, crystalline salts of quinoline carboxamides and methods for preparing crystalline salts of quinoline carboxamides are described in the International Application No. PCT/EP2005/050485, published as WO 2005/074899.

The use of various quinoline carboxamides for the treatment of cancer, more particularly solid cancers, such as prostate cancer and breast cancer, was disclosed in International Application No. PCT/SE00/02055, published as WO 01/30758. It has been found that these compounds bind to and inhibit the interactions of an immunomodulatory protein (S100A9), which protein promotes tumor development, influences suppressive and pro-angiogenic cells in the tumor microenvironment and participates in the establishment of pre-metastatic niches.

Tasquinimod has undergone trials for oral treatment of castrate resistant prostate cancer (CRPC) metastatic to the bone but was recently found to lack a sufficient effect on overall survival in this type of cancer.

The general term "cancer" covers a large number of malignant diseases, which may be classified in two ways: by the type of tissue in which the cancer originates (histological type) and by primary site, or the location in the body where the cancer first developed. The international standard for the classification and nomenclature of histologies is the International Classification of Diseases for Oncology, Third Edition (ICD-O-3). From a histological standpoint the cancers may be grouped into six major categories, viz. carcinoma, sarcoma, myeloma, leukemia, lymphoma and so-called mixed types.

Multiple myeloma (MM) is a cancer of plasma cells in the bone marrow. Normally, plasma cells produce antibodies and play a key role in immune function. In MM, collections of abnormal plasma cells accumulate in the bone marrow and interfere with the production of normal blood cells. Symptoms of MM are skeletal (bone) pain and fractures, anemia, infections, and other complications, such as polyneuropathy and renal insufficiency. MM is the second most common hematological malignancy, and still its exact causes remain unknown.

MM is normally treated using chemotherapy, which may optionally be followed by autologous stem cell transplantation (SCT).

In SCT, stem cells are removed from the patient, and are frozen and stored. Usually the patient first has undergone a high-dose chemotherapy, which destroys both healthy cells in the bone marrow and the plasma cells causing the disease, after which the removed stem cells are returned to the patient, to produce new, healthy blood cells in the bone marrow. A patient having undergone a SCT usually must take maintenance therapy for up to 2 years, e.g. with thalidomide or lenalidomide. SCT does not cure MM, it can only lead to longer survival. Furthermore, SCT can cause serious complications, especially vulnerability to infections.

MM also may be treated by chemotherapy only, in particular in patients at higher risk for complications from SCT. In that case, the chemotherapy drug often is used in combination with other drugs to reduce chemotherapy side effects, such as corticosteroids. Finally, MM also may be treated by radiation therapy.

Presently, MM is not considered curable. In 2010, less than 45% of US patients with diagnosed MM survived for more than 5 years after diagnosis, according to data from the National Cancer Institute at the National Institute of Health. It is obvious that there still remains an urgent need for new treatment options for MM.

SUMMARY OF THE INVENTION

One aspect is a compound of formula (I)

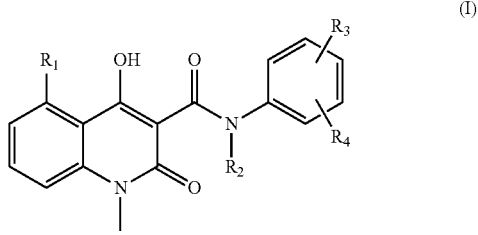

or a pharmaceutically acceptable salt thereof, wherein
$R_1$ is selected from hydrogen, methyl, ethyl, n-propyl, iso-propyl, methoxy, ethoxy, fluoro, chloro, bromo, trifluoromethyl, and trifluoromethoxy;
$R_2$ is C1-C4 alkyl;
$R_3$ is selected from methyl, methoxy, fluoro, chloro, bromo, trifluoromethyl, and trifluoromethoxy; and R$_4$ is selected from hydrogen, fluoro and chloro, with the proviso that R$_4$ is selected from fluoro and chloro only when R$_3$ is selected from fluoro and chloro; for use in the treatment of multiple myeloma.

In some embodiments, the treatment is performed by administration to a mammal subject, such as a human, of an amount of from 0.001 mg to 0.2 mg of the compound of formula (I)/kg of body weight per day, or of a corresponding amount of a pharmaceutically acceptable salt thereof.

Preferably, the administration is oral, but it also may be e.g. rectal, or parenteral, e.g. by injection, such as subcutaneous, intramuscular or intravenous injection.

In some embodiments, the treatment further comprises radiation therapy. In some embodiments, the treatment further comprises autologous stem cell transplantation.

In a second aspect, the use of the compound of formula (I) or a pharmaceutically acceptable salt thereof is provided, for the manufacturing of a medicament for the treatment of multiple myeloma.

Another aspect is a method of treatment of multiple myeloma comprising administering to a mammal subject, in particular a human subject, in need of such treatment, a therapeutically effective amount of a compound of formula (I) or a pharmaceutically acceptable salt thereof.

In some embodiments, the compound of formula (I) is 4-hydroxy-5-methoxy-N,1-dimethyl-2-oxo-N-[4-(trifluoromethyl)phenyl]-1,2-dihydroquinoline-3-carboxamide (tasquinimod) or a pharmaceutically acceptable salt thereof

DETAILED DESCRIPTION OF THE INVENTION

Definitions

Figure 1:
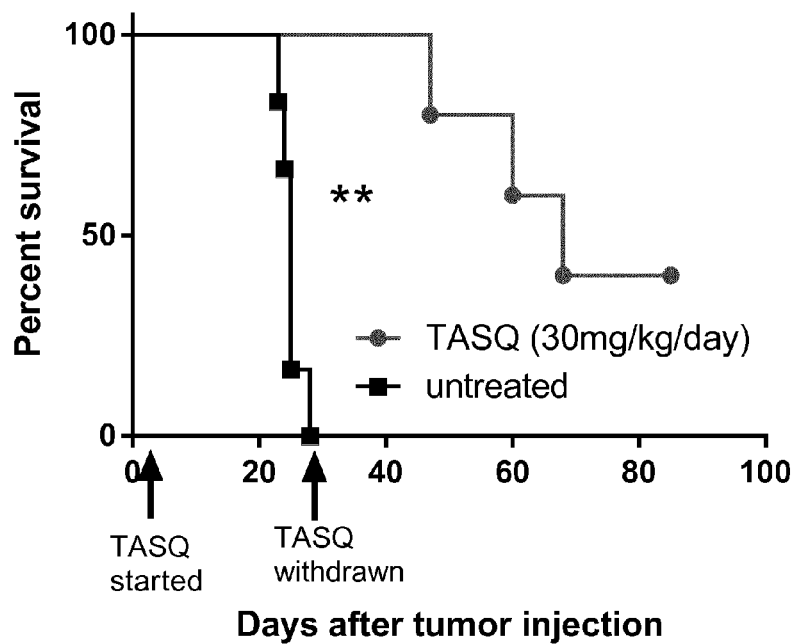
FIG. 1 is a graph showing percent survival as a function of time, in a multiple myeloma mouse model. 6-8 week old F1 progeny from FVB/NxC57BL/6 mice were iv injected with DP42 multiple myeloma tumor cells. Starting the next day, they received 30 mg/kg/day tasquinimod in drinking water which was withdrawn on day 30.

It should be noted that there are several synonymous terms designating the disease "multiple myeloma", i.e. Kahler disease, myeloma, myelomatosis, plasma cell dyscrasia and plasma cell myeloma. For the purpose of the present invention, these terms are all considered to be interchangeable with the term multiple myeloma.

"Optional" or "optionally" means that the subsequently described event or circumstance may but need not occur, and that the description includes instances where the event or circumstance occurs and instances in which it does not.

"Pharmaceutically acceptable" means that which is useful in preparing a pharmaceutical composition that is generally safe, non-toxic, and neither biologically nor otherwise undesirable and includes that which is acceptable for veterinary use as well as human pharmaceutical use.

Examples of pharmaceutically acceptable salts comprise salts with (as counter ion) an alkali metal ion, e.g. Li$^+$, Na$^+$ or K$^+$ or with an alkaline earth metal ion, e.g. Mg$^{2+}$ or Ca$^{2+}$, or with any other pharmaceutically acceptable metal ion, e.g. Zn$^{2+}$ or Al$^{3+}$; or pharmaceutically acceptable salts formed with organic bases, such as diethanolamine, ethanolamine, N-methylglucamine, triethanolamine or tromethamine.

"Therapeutically effective amount" means an amount of a compound of formula (I) or a pharmaceutically salt thereof, that, when administered to a subject for treating a disease state (here: MM), is sufficient to effect such treatment for the disease state. The "therapeutically effective amount" will vary depending on e.g. the age and relative health of the treated subject, the state of progression of the MM, the route and form of administration, the possible additional use of other drugs, e.g. in a combination therapy, etc.

As used herein the terms "treatment" or "treating" is an approach for obtaining beneficial or desired results including clinical results. Beneficial or desired clinical results can include, but are not limited to, alleviation or amelioration of one or more symptoms of MM ("the disease"), diminishment of extent of the disease, stabilization (i.e., not worsening) of the state of the disease, preventing spread of the disease, delay or slowing of progression of the disease, amelioration or palliation of the disease state, and remission (whether partial or total), whether detectable or undetectable. The term can also mean prolonging survival as compared to expected survival without the treatment.

Common symptoms of MM are bone pain due to lytic bone disease, weakness and fatigue due to anemia, weight loss, confusion, excessive thirst, constipation due to hypercalcemia, kidney problems, infections due to non-functioning immunoglobulins. More uncommon symptoms comprise accumulation of plasma cells in purplish lumps visible underneath the skin, so called extramedullary plasmacytomas.

The term "mammal" refers to a human or any mammalian animal, e.g. a primate, a farm animal, a pet animal, or a laboratory animal. Preferably, the mammal is a human.

The mammal (e.g. human) subject that may suitably be treated according to the present invention may be one suffering from MM, or one at (increased) risk of developing MM. There are patients suffering from certain other conditions that have an increased risk of developing MM. Such conditions are monoclonal gammopathy of uncertain significance (MGUS) and solitary plasmacytoma. In fact, these conditions may even be early forms of MM. Therefore, in some embodiments, the term MM also includes a condition selected from monoclonal gammopathy of uncertain significance (MGUS) and solitary plasmacytoma.

The term "C1-C4 alkyl" refers to a branched or unbranched alkyl group having from 1, 2, 3 or 4 carbon atoms, i.e. methyl, ethyl, n-propyl, isopropyl, n-butyl, sec-butyl, isobutyl or tert-butyl.

The term methoxy refers to the moiety MeO—, or $CH_3O$—.

The term ethoxy refers to the moiety EtO—, or $CH_3CH_2O$—.

The terms fluoro, chloro and bromo also may be represented by F, Cl and Br.

The term trifluoromethyl refers to the moiety $CF_3$—.

The term trifluoromethoxy refers to the moiety $CF_3O$—.

As noted herein above, the compound for use according to the invention is a compound of formula (I)

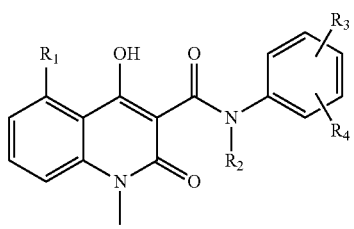

(I)

or a pharmaceutically acceptable salt thereof,
as defined herein above.

In the compound of formula (I), $R_1$ is selected from H, methyl, ethyl, n-propyl, iso-propyl, methoxy, ethoxy, fluoro, chloro, bromo, trifluoromethyl, and trifluoromethoxy. In some embodiments, $R_1$ is selected from methyl, ethyl, n-propyl, iso-propyl, methoxy, ethoxy, fluoro, chloro, bromo, trifluoromethyl, and trifluoromethoxy. In some other embodiments, $R_1$ is selected from ethyl, n-propyl, iso-propyl, methoxy, ethoxy, chloro, bromo, trifluoromethyl, and trifluoromethoxy. In still other embodiments, $R_1$ is selected from ethyl, methoxy, chloro, and trifluoromethyl. In some particular embodiments, $R_1$ is methoxy.

The moiety $R_2$ is a C1-C4 alkyl radical, which radical may be branched or linear. In some embodiments, $R_2$ is a C1-C3 alkyl radical. In some embodiments, $R_2$ is methyl or ethyl. In some particular embodiments, $R_2$ is methyl.

The moiety $R_3$ is selected from methyl, methoxy, fluoro, chloro, bromo, trifluoromethyl, and trifluoromethoxy. In some embodiments, $R_3$ is selected from methyl, methoxy, fluoro, chloro, trifluoromethyl, and trifluoromethoxy. In some particular embodiments, $R_3$ is trifluoromethyl.

$R_4$ is selected from hydrogen, fluoro and chloro, with the proviso that $R_4$ is selected from fluoro and chloro only when $R_3$ is selected from fluoro and chloro. In some embodiments, $R_4$ is hydrogen or fluoro. In some particular embodiments, $R_4$ is hydrogen.

In some particular embodiments, in a compound of formula (I),
$R_1$ and $R_4$ are as defined herein above;
$R_2$ is methyl or ethyl, in particular methyl; and
$R_3$ is selected from methyl, methoxy, fluoro, chloro, trifluoromethyl, and trifluoromethoxy.

In some other particular embodiments, in a compound of formula (I),
$R_1$ is as defined herein above;
$R_2$ is methyl or ethyl, in particular methyl;
$R_3$ is selected from methyl, methoxy, fluoro, chloro, trifluoromethyl, and trifluoromethoxy; and
$R_4$ is H.

In some embodiments, $R_3$ is in para-position, i.e. the compound for use as defined herein may be represented by formula (Ia)

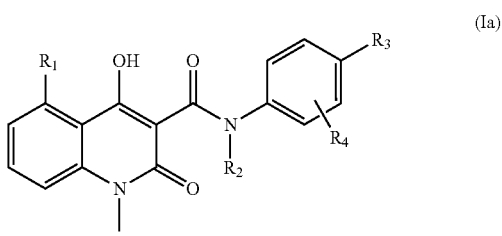

(Ia)

wherein $R_1$, $R_2$, $R_3$ and $R_4$ are as defined herein above.

For example, in some embodiments of a compound of formula (Ia),
$R_1$ and $R_4$ are as defined herein above;
$R_2$ is methyl or ethyl, in particular methyl; and
$R_3$ is selected from methyl, methoxy, fluoro, chloro, trifluoromethyl, and trifluoromethoxy.

In some other particular embodiments, in a compound of formula (Ia),
$R_1$ is as defined herein above;
$R_2$ is methyl or ethyl, in particular methyl;
$R_3$ is selected from methyl, methoxy, fluoro, chloro, trifluoromethyl, and trifluoromethoxy; and
$R_4$ is H.

As noted herein above, in some embodiments, $R_4$ is hydrogen. In those embodiments, the compound of formula (I) may be represented by formula (Ib)

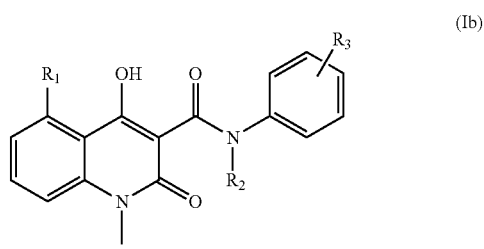

(Ib)

wherein $R_1$, $R_2$ and $R_3$ are as defined herein above.

For example, in some embodiments of a compound of formula (Ib),
$R_1$ is as defined herein above;
$R_2$ is methyl or ethyl, in particular methyl; and
$R_3$ is selected from methyl, methoxy, fluoro, chloro, trifluoromethyl, and trifluoromethoxy.

In some particular embodiments of a compound of formula (I), $R_3$ is in para-position and $R_4$ is H, and the compound for use as defined herein may then be represented by formula (Ic)

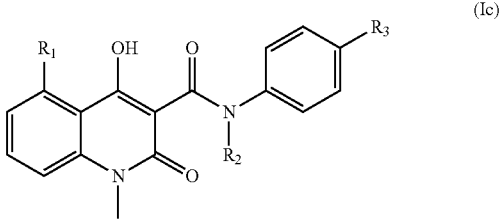

(Ic)

wherein $R_1$, $R_2$ and $R_3$ are as defined herein above.

In some particular embodiments of a compound of formula (Ic), $R_1$ is as defined herein;

$R_2$ is methyl or ethyl, in particular methyl; and $R_3$ is selected from methyl, methoxy, fluoro, chloro, trifluoromethyl, and trifluoromethoxy.

For the purpose of the present invention, any reference to a compound of formula (I) also should be understood as a reference to a compound of any one of the formulas (Ia), (Ib) and (Ic), unless otherwise specified or apparent from the context.

In one embodiment, the compound of formula (I) is 4-hydroxy-5-methoxy-N,1-dimethyl-2-oxo-N-[4-(trifluoromethyl)phenyl]-1,2-dihydroquinoline-3-carboxamide (tasquinimod), of the structural formula:

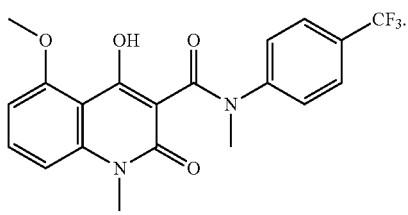 [SMILES: COc1cccc2c1c(O)c(C(=O)N(C)c1ccc(C(F)(F)F)cc1)c(=O)n2C]

As mentioned herein above, compounds of formula (I), pharmaceutically acceptable salts thereof, deuterated forms thereof, crystalline salts thereof, and pharmaceutical compositions containing the compounds and their salts, as well as methods for preparing such compounds, their salts, deuterated forms and pharmaceutical compositions containing the compounds and their salts have been described in WO 99/55678, WO 00/03991, WO 03/106424, WO 2005/074899, WO 2012/004338 and WO 2012/175541 (vide supra), which documents are hereby incorporated by reference in their entireties into the present application.

In some embodiments, any reference to a compound of formula (I) also encompasses the deuterated form of thereof. As mentioned herein above, a deuterated form of tasquinimod is described in WO 2012/175541. The person of ordinary skill in the art will be capable of preparing analogously deuterated compounds of formula (I) by following the description provided in said WO pamphlet. In some embodiments, thus, the compound of formula (I) has a deuterium enrichment in the moiety $R_2$ of formula (I) of at least 70%, more preferably at least 90%. For example, in some embodiments, $R_2$ is methyl having a deuterium enrichment of at least 70%, more preferably at least 90%.

In some particular embodiments, the compound of formula (I) is tasquinimod having a deuterium enrichment in the amide-N methyl group of at least 70%, more preferably at least 90%.

In some other embodiments, the compound of formula (I) is non-deuterated, having a deuterium content corresponding to the natural abundance of deuterium.

The present invention includes the compound of formula (I) or a pharmaceutically acceptable salt thereof, formulated in a pharmaceutical composition, optionally together with a pharmaceutically acceptable excipient, e.g. a carrier, for use in the treatment of multiple myeloma.

The pharmaceutical composition may be suitable for enteral administration, such as rectal or oral administration, or for parenteral administration, to a mammal (especially a human), and comprises a therapeutically effective amount of a compound of formula (I) or a pharmaceutically acceptable salt thereof, as active ingredient, optionally in association with a pharmaceutically acceptable excipient, e.g. a pharmaceutically acceptable carrier. The therapeutically effective amount of the active ingredient is as defined herein above and depends e.g. on the species of mammal, the body weight, the age, the individual condition, individual pharmacokinetic data, and the mode of administration.

For enteral, e.g. oral, administration, the compound of formula (I) may be formulated in a wide variety of dosage forms. The pharmaceutically acceptable carriers may be either solid or liquid. Solid form preparations include powders, tablets, pills, lozenges, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions, or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well-known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

Exemplary compositions for rectal administration include suppositories which can contain, for example, a suitable non-irritating excipient, such as cocoa butter, synthetic glyceride esters or polyethylene glycols, which are solid at ordinary temperatures, but liquefy and/or dissolve in the rectal cavity to release the drug.

The compound of formula (I) also may be administered parenterally, e.g. by injection or infusion, e.g. by intravenous, intraarterial, intraosseous, intramuscular, intracerebral, intracerebroventricular, intrasynovial, intrasternal, intrathecal, intralesional, intracranial, intratumoral, intracutaneous and subcutaneous injection or infusion. Thus, for parenteral administration, the pharmaceutical compositions may be in the form of a sterile injectable or infusible preparation, for example, as a sterile aqueous or oleaginous suspension. This suspension may be formulated according to techniques known in the art using suitable dispersing or wetting agents (e.g., Tween 80), and suspending agents. The sterile injectable or infusible preparation may also be a sterile injectable or infusible solution or suspension in a non-toxic parenterally acceptable diluent or solvent. For example, the pharmaceutical composition may be a solution in 1,3-butanediol. Other examples of acceptable vehicles and solvents that may be employed in the compositions of the present invention include, but are not limited to, mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant.

Solutions for parenteral use also may contain suitable stabilizing agents, and if necessary, buffer substances. Suitable stabilizing agents include antioxidizing agents, such as sodium bisulfate, sodium sulfite or ascorbic acid, either alone or combined, citric acid and its salts and sodium EDTA. Parenteral solutions may also contain preservatives, such as benzalkonium chloride, methyl- or propyl-paraben, and chlorobutanol.

Conventional procedures for the selection and preparation of suitable pharmaceutical formulations are described, for example, in "Pharmaceutics—The Science of Dosage Form Design", M. B. Aulton, Churchill Livingstone, $2^{nd}$ ed. 2002 (ISBN 0443055173, 9780443055171). Suitable pharmaceutical excipients, e.g. carriers, and methods of preparing pharmaceutical dosage forms also are described in Remington's Pharmaceutical Sciences, Mack Publishing Company, a standard reference text in art of drug formulation.

The pharmaceutical compositions may comprise from approximately 1% to approximately 95%, preferably from approximately 20% to approximately 90% of a compound of formula (I), together with at least one pharmaceutically acceptable excipient. In general, the compounds of formula (I) will be administered in a therapeutically effective amount by any of the accepted modes of administration for agents that serve similar utilities.

While e.g. injection or rectal administration of a compound of formula (I) may be contemplated if necessary, oral administration generally is considered the most convenient.

The dosage level and frequency will generally be as determined by the treating physician, with due regard to factors such as and the sex, age, corporal weight and relative health of the treated subject, the state of progression of the MM, the selected route and form of administration, the additional use of other drugs, e.g. in a combination therapy.

Generally, a daily dosage ranging from a minimum of 0.001 mg/kg body weight, or 0.002 mg/kg body weight or 0.005 mg/kg body weight or 0.01 mg/kg body weight, to a maximum of 0.2 mg/kg body weight, or 0.1 mg/kg body weight, or 0.05 mg/kg body weight, or 0.02 mg/kg body weight is contemplated.

In one embodiment, the compound of formula (I) is administered in an amount of 0.05 to 0.15 mg/day, or 0.08 to 0.1 mg/day, e.g. 0.1 mg/day.

In one embodiment, the compound of formula (I) is administered in an amount of 0.1 to 0.3 mg/day, or 0.15 to 0.25 mg/day, e.g. 0.2 mg/day.

In one embodiment, the compound of formula (I) is administered in an amount of 0.1 to 1 mg/day, or 0.2 to 0.8 mg/day, e.g. 0.5 mg/day.

In one embodiment, the compound of formula (I) is administered in an amount of 0.2 to 1.5 mg/day, or 0.4 to 1.2 mg/day, e.g. 0.8 mg/day.

In one embodiment, the compound of formula (I) is administered in an amount of 0.5 to 2 mg/day, or 0.8 to 1.2 mg/day, e.g. 1 mg/day.

In one embodiment, the compound of formula (I) is administered in an amount of 0.8 to 3 mg/day, or 1 to 2.5 mg/day, e.g. 2 mg/day.

In one embodiment, the compound of formula (I) is administered in an amount of 1 to 6 mg/day, or 2 to 4 mg/day, e.g. 3 mg/day.

In some embodiments, the dosage may be gradually adjusted to reach optimal results, so-called dosage titration. For example, dosage titration may comprise starting with a low daily dosage of e.g. 0.25 mg and maintaining this dose level for a period of 1 or 2 weeks. In case no significant side effects are encountered that may contraindicate raising the dose, the level may then be increased, e.g. to 0.5 mg/day for 1 or 2 weeks, after which period another increase may be contemplated, to reach a daily dosage of 1 mg, and so on. In such a method, if any significant side effects occur after an incremental increase of the dosage, the dosage may again be reduced to a previous level.

Side effects that may occur include those that may generally be encountered in this type of treatment, e.g. gastrointestinal problems, tiredness, and flu-like syndrome, considered to be related to dosage.

The compound of formula (I) preferably is administrated on a daily basis, e.g. 1-3 times a day, or 1-2 times a day, such as once daily. In some embodiments, the drug is administrated on a less frequent basis, e.g. every two days, once a week etc.

It should also be noted that if a pharmaceutically acceptable salt of the compound of formula (I) is administered, an equivalent dosage would be one resulting in the indicated dosage of the compound in non-salt form.

The above information and embodiments generally also apply to pharmaceutically acceptable salts of the compound of formula (I), unless otherwise specifically indicated or apparent from the context.

EXAMPLES

Herein below the invention will be further illustrated by a number of non-limiting examples.

In Examples 1-3, statistical analysis was done using GraphPad Prism® software. Difference in mice survival was evaluated by log-rank (Mantel-Cox) test. Difference in tumor growth was analyzed by 2-way ANOVA.

Statistical significance: *–$p<0.05$; –$p<0.005$; and *–$p<0.001$.

Example 1

DP42 multiple myeloma tumors were established in syngeneic 6-8 week old mice (F1 progeny from FVB/NxC57BL/6; cf. J Immunol. 2013 Apr. 1; 190(7):3815-23).

Figure 2:
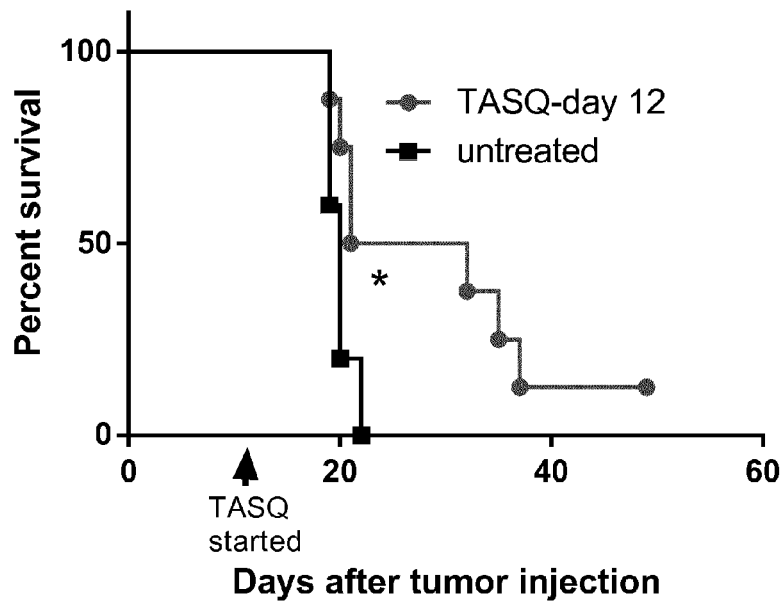
FIG. 2 is a graph showing percent survival as a function of time, in a multiple myeloma mouse model. 6-8 week old F1 progeny from FVB/NxC57BL/6 mice were iv injected with DP42 multiple myeloma tumor cells. Mice started receiving tasquinimod in drinking water on day 12 after DP42 injection when the tumor (CD138+) in the bone marrow was ~5-7%

One day after tumor cell injection, mice were split into 2 groups and were either treated with tasquinimod given in drinking water at a dose of 30 mg/kg/day (n=5) or received drinking water without tasquinimod (n=6). Tasquinimod was withdrawn on day 30 (FIG. 1). Survival of mice was monitored. In another experiment, treatment with tasquinimod (n=8) started on day 12 after DP42 tumor cell injection. Control group (n=5) received drinking water without tasquinimod. Survival of mice was monitored (FIG. 2).

Figure 3A:
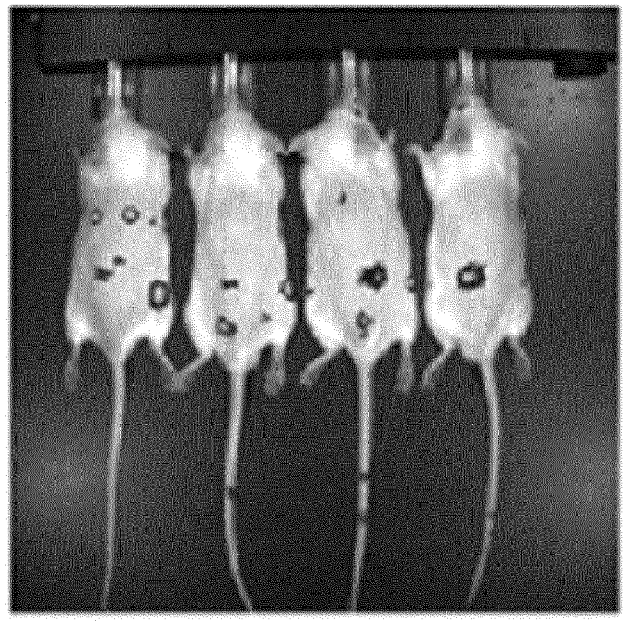
FIG. 3 shows IVIS images of 6-8 week old F1 progeny from FVB/NxC57BL/6 mice injected with DP42-luciferase cells and (A) treated with 30 mg/kg/day of tasquinimod in drinking water starting on the day after injection or (B) receiving no tasquinimod. The IVIS images were taken on day 13 after tumor injection.
Figure 3B:
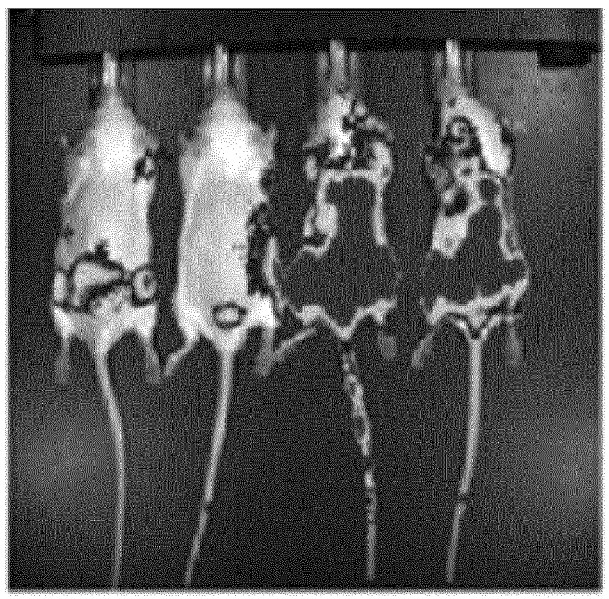

Luciferase-expressing DP42 multiple myeloma tumor cells were injected iv. Tasquinimod treatment was started the next day and tumor growth was imaged by IVIS on day 13 after tumor injection (FIGS. 3A and B).

Example 2

Figure 4:
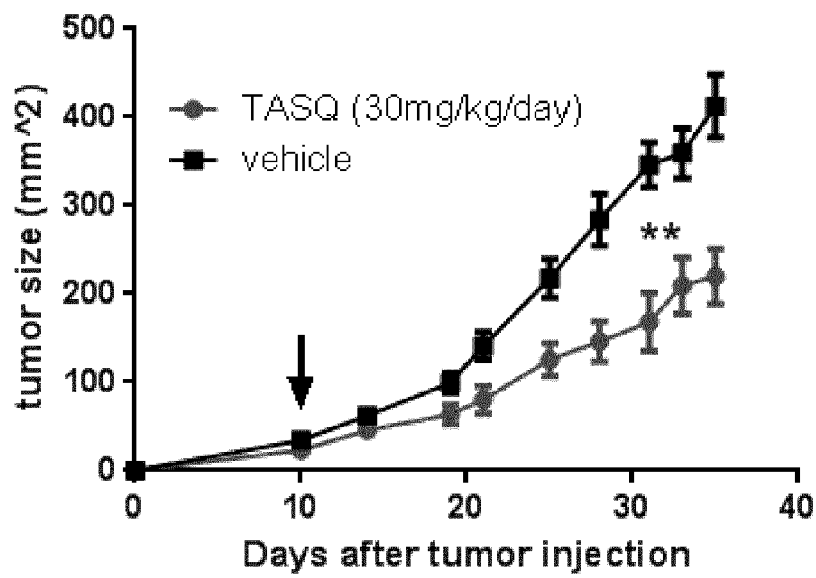
FIG. 4 is a graph showing tumor size (in mm$^2$) as a function of time, in SCID-Beige mice injected with human MM cell line H929 subcutaneously and receiving tasquinimod (30 mg/kg/day) from day 10, or receiving only vehicle.
Figure 5:
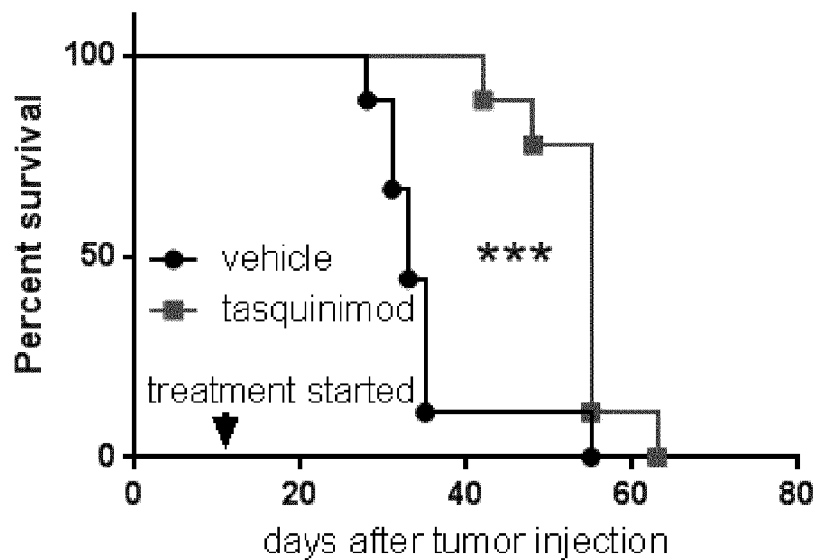
FIG. 5 is a graph showing the percent survival as a function of time, of SCID-Beige mice injected with human MM cell line H929 subcutaneously and receiving tasquinimod (30 mg/kg/day) from day 10, or receiving only vehicle.

6-8 weeks old SCID-beige mice were inoculated subcutaneously in the right flank with $5 \times 10^6$ NCI-H929 cells (cf. Blood. 2008 Feb. 15; 111(4):2220-9) in 100 µL phosphate-buffered saline (PBS). Ten days after tumor cell injection, mice were assigned to the treatment (n=7) or control (n=9) groups. Treatment group received tasquinimod at a dose of 30 mg/kg/day. Tumor size was monitored twice a week (FIG. 4). Mice were euthanized when tumor reached 400 mm$^2$, and time to endpoint was monitored and plotted (FIG. 5). Difference in tumor growth was evaluated by 2-way ANOVA. Differences in survival were analyzed by log-rank test.

Example 3

Figure 6:
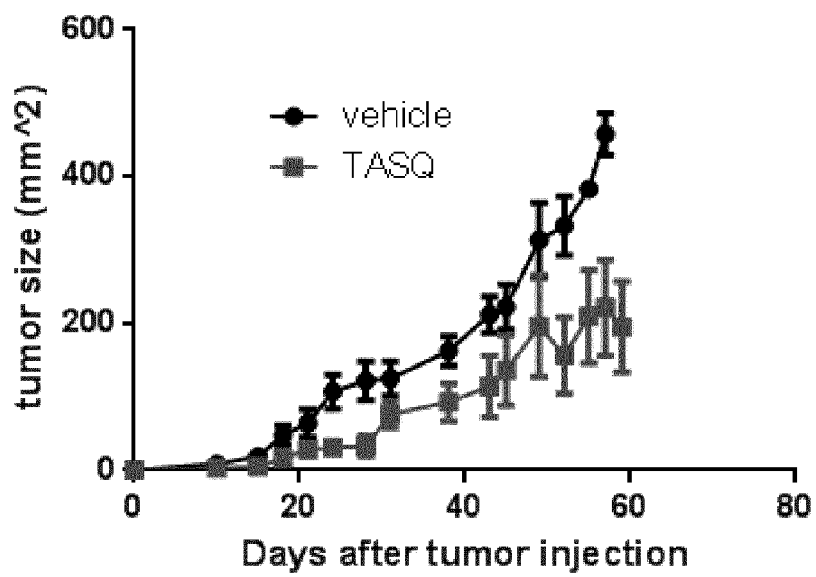
FIG. 6 is a graph showing tumor size (in mm$^2$) as a function of time, in SCID-Beige mice injected with human MM cell line 8226 subcutaneously and receiving tasquinimod (30 mg/kg/day) from day 15, or receiving only vehicle.
Figure 7:
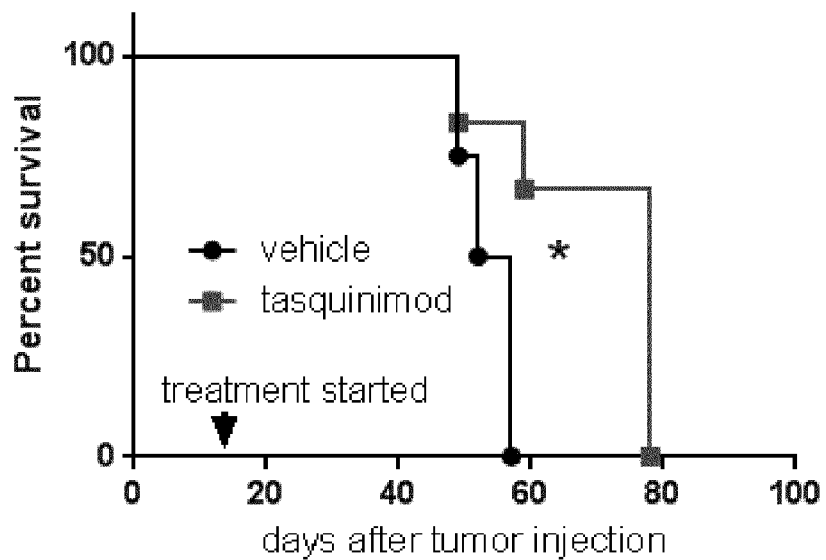
FIG. 7 is a graph showing the percent survival as a function of time, of SCID-Beige mice injected with human MM cell line 8226 subcutaneously and receiving tasquinimod (30 mg/kg/day) from day 15, or receiving only vehicle.

6-8 weeks old SCID-beige mice were inoculated subcutaneously in the right flank with $10 \times 10^6$ RPMI-8226 cells (cf. Blood, 2008; Feb. 15; 111(4):2220-9) in 100 µL phosphate-buffered saline (PBS). Fifteen days after tumor cell injection mice were assigned to the treatment (n=4) or control (n=6) groups. Treatment group received tasquinimod at a dose of 30 mg/kg/day. Tumor size was monitored twice a week (FIG. 6). Mice were euthanized when tumor reached 400 mm$^2$, and time to endpoint was monitored and plotted (FIG. 7). Differences in survival were analyzed by log-rank test.

The invention claimed is:

1. A method of treatment of multiple myeloma by administration to a mammal in need thereof of a compound of formula (I)

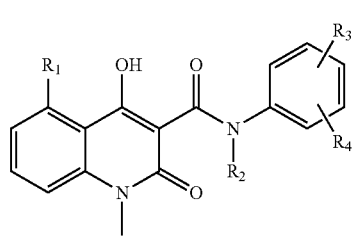

(I)

or a pharmaceutically acceptable salt thereof, wherein $R_1$ is selected from hydrogen, methyl, ethyl, n-propyl, iso-propyl, methoxy, ethoxy, fluoro, chloro, bromo, trifluoromethyl, and trifluoromethoxy;

$R_2$ is C1-C4 alkyl;

$R_3$ is selected from methyl, methoxy, fluoro, chloro, bromo, trifluoromethyl, and trifluoromethoxy; and $R_4$ is selected from hydrogen, fluoro and chloro, with the proviso that $R_4$ is selected from fluoro and chloro only when $R_3$ is selected from fluoro and chloro.

2. The method according to claim 1, wherein $R_2$ is methyl or ethyl.

3. The method according to claim 1, wherein $R_3$ is in para-position and is selected from methyl, methoxy, fluoro, chloro, trifluoromethyl, and trifluoromethoxy.

4. The method according to claim 1, wherein $R_4$ is hydrogen.

5. The method according to claim 1, wherein the compound is 4-hydroxy-5-methoxy-N,1-dimethyl-2-oxo-N-[4-(trifluoromethyl)phenyl]-1,2-dihydroquinoline-3-carboxamide.

6. The method according to claim 1, wherein the treatment is by oral administration.

7. The method according to claim 1, wherein the treatment is by administration of an amount of from 0.001 mg to 0.2 mg of the compound/kg of body weight per day, or of a corresponding amount of the pharmaceutically acceptable salt.

8. The method according to claim 1, wherein the treatment is by administration of the compound or salt 1-3 times a day.

9. The method according to claim 1, wherein the compound or salt is administered in a solid or semi-solid dosage form.

10. The method according to claim 9, wherein the solid or semi-solid dosage form is a capsule, a tablet or a pill.

11. The method according to claim 1, wherein the compound or salt is administered dissolved or suspended in a liquid vehicle.

12. The method according to claim 1, wherein the treatment further comprises radiation therapy and/or autologous stem cell transplantation.

13. The method according to claim 1, wherein the treatment is performed by administration of the compound or salt to a mammal suffering from multiple myeloma or a mammal at risk of developing multiple myeloma.

14. The method according to claim 5, wherein the treatment is by oral administration.

15. The method according to claim 5, wherein the treatment is by administration of an amount of from 0.001 mg to 0.2 mg of the compound/kg of body weight per day, or of a corresponding amount of the pharmaceutically acceptable salt.

16. The method according to claim 5, wherein the treatment is by administration of the compound or salt 1-3 times a day.

17. The method according to claim 5, wherein the compound or salt is administered in a solid or semi-solid dosage form.

18. The method according to claim 17, wherein the solid or semi-solid dosage form is a capsule, a tablet or a pill.

19. The method according to claim 5, wherein the compound or salt is administered dissolved or suspended in a liquid vehicle.

20. The method according to claim 5, wherein the treatment further comprises radiation therapy and/or autologous stem cell transplantation.

* * * * *